(12) United States Patent
Chiang et al.

(10) Patent No.: US 9,526,478 B2
(45) Date of Patent: Dec. 27, 2016

(54) CORD BLOOD PERFUSION AND COLLECTION SYSTEM

(71) Applicant: THE JOHNS HOPKINS UNIVERSITY, Baltimore, MD (US)

(72) Inventors: Christopher Kerway Chiang, Baltimore, MD (US); Matthew Stephen Means, Punxsutawney, PA (US)

(73) Assignee: The Johns Hopkins University, Baltimore, MD (US)

( * ) Notice: Subject to any disclaimer, the term of this patent is extended or adjusted under 35 U.S.C. 154(b) by 144 days.

(21) Appl. No.: 14/113,838

(22) PCT Filed: Dec. 21, 2012

(86) PCT No.: PCT/US2012/071134
§ 371 (c)(1),
(2) Date: Oct. 25, 2013

(87) PCT Pub. No.: WO2013/096719
PCT Pub. Date: Jun. 27, 2013

(65) Prior Publication Data
US 2014/0303517 A1    Oct. 9, 2014

Related U.S. Application Data

(60) Provisional application No. 61/579,268, filed on Dec. 22, 2011.

(51) Int. Cl.
*A61B 19/00* (2006.01)
*A61B 10/00* (2006.01)
(Continued)

(52) U.S. Cl.
CPC ......... *A61B 10/0045* (2013.01); *A61B 5/1411* (2013.01); *A61B 5/150038* (2013.01);
(Continued)

(58) Field of Classification Search
CPC . A61B 10/0045; A61B 5/1411; A61B 5/1405; A61B 5/150038; A61B 5/150045; A61B 5/15003; A61B 17/42; A61J 1/10
See application file for complete search history.

(56) References Cited

U.S. PATENT DOCUMENTS 5,690,646 A * 11/1997 Gruenberg ........... A61B 5/1405
600/573
5,919,176 A * 7/1999 Kuypers .............. A61B 5/1405
604/317

(Continued)

*Primary Examiner* — Philip R Wiest
(74) *Attorney, Agent, or Firm* — Johns Hopkins Technology Ventures

(57) ABSTRACT

An embodiment in accordance with the present invention provides a device and method for collecting cord blood from the umbilical cord and placenta. The device includes a vascular access device, a portable tray container, and a perfusion pump device. The vascular access device includes two vascular access components (VACs) that clamp onto the umbilical cord at the time of delivery to accurately guide cannulation of the vein. After clamping on the VACs, the placenta and VACs are placed into the portable tray container. The portable tray container is a closable and disposable container which features a dock for accepting the VACs and impaling the umbilical vein for vascular access. The dock is also connected to perfusate and collection bags, located on the outside surfaces of the tray. The tray and perfusate and collection bags interfaced with the perfusion pump device to flush out and collect the stem cells from the umbilical cord and placenta.

18 Claims, 10 Drawing Sheets

(51) Int. Cl.
   *A61J 1/10*    (2006.01)
   *A61B 5/15*    (2006.01)
   *A61B 17/42*   (2006.01)

(52) U.S. Cl.
   CPC .. *A61B 5/150045* (2013.01); *A61B 5/150229* (2013.01); *A61B 5/150305* (2013.01); *A61B 5/150366* (2013.01); *A61B 17/42* (2013.01); *A61J 1/10* (2013.01); *A61B 5/15003* (2013.01)

(56) References Cited

U.S. PATENT DOCUMENTS

| | | |
|---|---|---|
| 7,131,958 B2 | 11/2006 | Deverre |
| 7,638,141 B2 * | 12/2009 | Hariri ................ C12N 5/0603 424/520 |
| 7,909,806 B2 | 3/2011 | Goodman et al. |
| 2008/0228153 A1 | 9/2008 | Shacham |
| 2008/0287829 A1 | 11/2008 | Moore et al. |

* cited by examiner

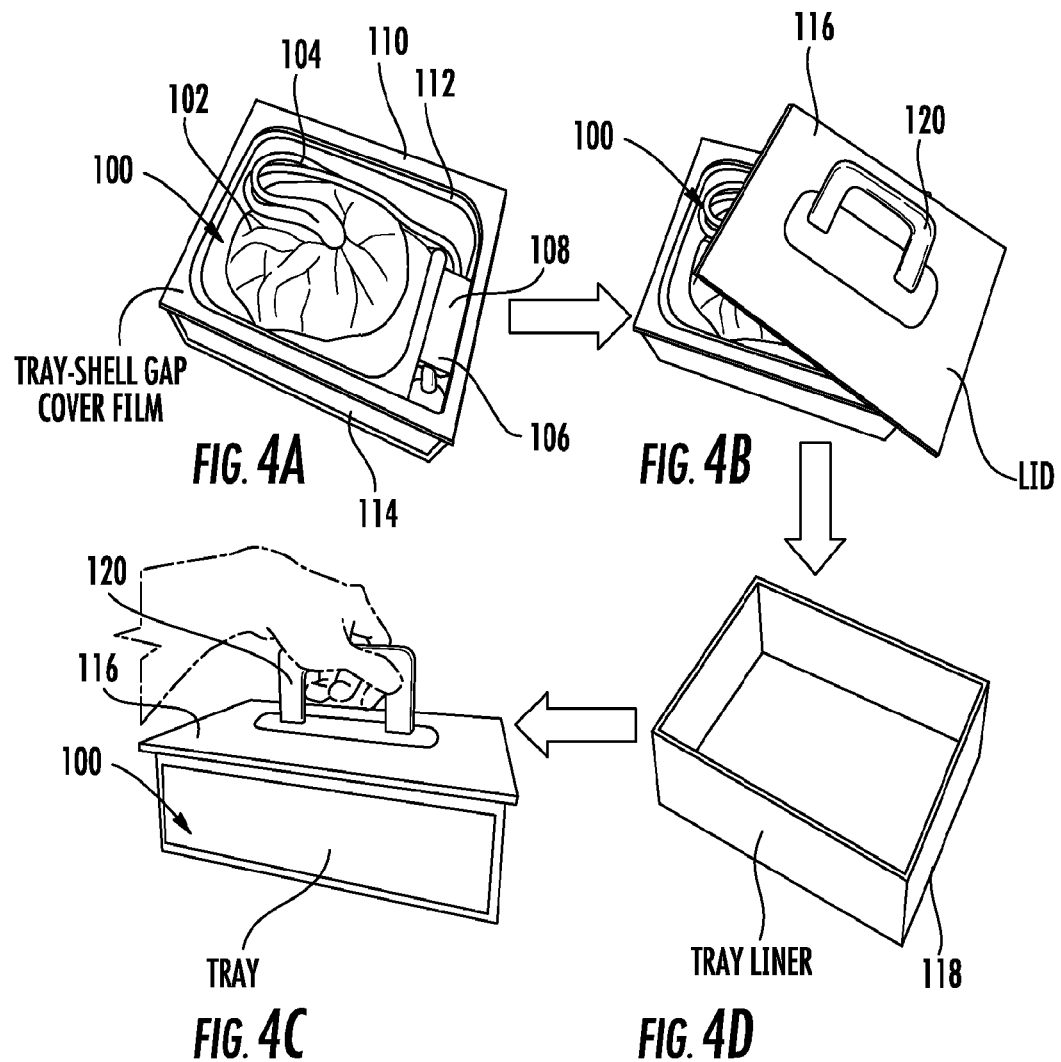

CORD BLOOD PERFUSION AND COLLECTION SYSTEM

CROSS-REFERENCE TO RELATED APPLICATIONS

This application is a 35 U.S.C. 371 U.S. national entry of International Application PCT/US2012/071134 having an international filing date of Dec. 21, 2012 which claims the benefit of U.S. Provisional Application No. 61/579,268 filed Dec. 22, 2011, the content of each of the aforementioned applications is herein incorporated by reference in its entirety.

FIELD OF THE INVENTION

The present invention relates generally to medical fluid collection. More particularly, the present invention relates to a device and method for collecting cord blood from the umbilical cord and placenta.

BACKGROUND OF THE INVENTION

Umbilical cord blood is an up-and-coming and readily-available source of transplantable hematopoietic stem cells unhindered by ethical issues or complex surgical extraction. It is collected from the umbilical cord and placenta after birth and used in the treatment of over 70 diseases, offering improved outcomes and replacing other graft sources when applicable. There are over 670 ongoing clinical trials examining potential cord blood therapies that collectively affect over 300 million people worldwide.

Currently, cord blood is banked privately, as fee-for-service, and publicly, similar to blood donations. Despite its potential, cord blood experiences limited adoption, and over 90% of cord blood in the US is discarded. One of the primary reasons for its underutilization is the ineffective collection method; the conventional, gravity-driven needle and blood bag is inefficient, highly dependent on user skill and patience, and consistently fails to collect sufficient quantities of cord blood stem cells. Because clinical outcomes are driven by cell dose per patient body weight, 60% of 2010's estimated 100,000 cord blood units (CBUs) collected for US public banking were discarded, as they did not contain enough total nucleated cells (TNC) to be deemed clinically relevant. Even banked units are almost always limited to pediatric therapies, with less than 10% of the banked inventory able to treat an adult of 150 lb. at the minimum recommended cell dose of $2.5 \times 10^7$ TNC/kg. Yet, over 90% of disease occurrence treated with cord blood takes place in adulthood.

These low cell yields have adversely affected the industry. Public banks operate by absorbing the costs of collection and processing ($425/unit) to store a CBU and sell it for an average of $35,000 for a transplant procedure. Public banks, however, struggle with unsustainable costs of an effective $122,000 per CBU sold, associated with banking unsellable (due to low TNC) units in the inventory. Public banks are further limited geographically in their collection sites due to the need to employ a skilled cord blood collection technician in an associated hospital to ensure the quality of collections. This results in lower supply and reduced demographic diversity.

Private banks offer families the option of banking a child's cord blood for exclusive family use for an average collection and annual storage fee of $1750 and $125, respectively. However, the market is saturated, and the low cell-yield of collection makes private banking an expensive, low value option. Excluding emerging therapies, the chances of a child utilizing cord blood by age 10 is 1 in 5,000.

It would therefore be advantageous to provide a system and method for collecting cord blood that is easy to use and maximizes the cell yield in collected samples.

SUMMARY OF THE INVENTION

The foregoing needs are met, to a great extent, by the present invention, wherein in one aspect, a device for collecting cord blood includes a first vascular access component configured to be clamped on an umbilical cord. The device also includes a tray defining a first chamber for receiving a placenta. The tray has a second chamber for receiving the first vascular access component, and the second chamber is configured to hold needles to puncture umbilical vessels for perfusing the placenta and umbilical cord and collecting the cord blood.

In accordance with an aspect of the present invention, the first vascular access component is configured to be clamped at a distal end of the umbilical cord, and a second vascular access component is configured to be clamped on the umbilical cord. The second vascular access component is further configured to be clamped at a proximal end of the umbilical cord, and positioned adjacent to a junction of the umbilical cord and the placenta attached to the umbilical cord. The tray comprises a third chamber for receiving the second vascular access component, and the third chamber is configured to hold needles to puncture the umbilical vessels for perfusing the placenta and umbilical cord and collecting the cord blood. The first and second vascular access components include aiming indicators to align with an anatomical feature of the umbilical cord. The anatomical feature further can take the form of an umbilical vein. The aiming indicators can take the form of a crosshair, a post, or a window.

In accordance with another aspect of the present invention, the first vascular access component includes one access point. Correspondingly, the second chamber for receiving the first vascular access component includes one needle. The second vascular access component can include two access points, and the third chamber for receiving the second vascular access component includes two needles. The device can also include a perfusion bag and a collection bag. The perfusion bag contains a saline solution and an anticoagulant, and the anticoagulant can be heparin or citrate phosphate dextrose. The device further includes a lid. The tray includes a means to seal the lid to the device. The lid is also configured to be deformable to provide a compressive force on the placenta for the purpose of driving cord blood out of the placental vasculature and into the umbilical cord. The first chamber for receiving the placenta can include sloped walls. Additionally, the device can include a removable tray shell, such that any contamination can be removed and disposed of before perfusion. The tray can also be configured to be coupled to a device for driving the perfusion process.

In accordance with another aspect of the present invention, a method of collecting cord blood includes positioning an umbilical cord in a first vascular access component. The method also includes cannulating umbilical vessels of the umbilical cord with guidance from a position of the first vascular access component. The placenta and the umbilical cord are perfused with a perfusate, and the perfusate and cord blood are collected.

In accordance with yet another aspect of the present invention, the method includes positioning a distal end of the umbilical cord in the first vascular access component. The method further includes locking a proximal end of the umbilical cord in a second vascular access component, just proximal to a juncture between the umbilical cord and its associated placenta. Additionally, the method includes cannulating the umbilical vessels of the umbilical cord with guidance from a position of the second vascular access component, and aligning an aiming indicator on the first and second vascular access components with the umbilical vein. The method can also include accessing the umbilical vein from a backside/non-outer surface, traversing through Wharton's jelly of the umbilical cord.

In accordance with still another aspect of the present invention, the method can include discarding a volume of the perfusate collected to discard low-cell content fluids that are collected during perfusion. The volume of the perfusate collected can be calculated using at least one of in-perfusate volume, delay prior to collecting, and prior perfusion cycles. Additionally, the method can include sterilizing the umbilical cord before perfusion. This can be accomplished using a wipe moistened with an antiseptic and disposed within the first vascular access component. The method can also include positioning the placenta, the umbilical cord, and the vascular access device in a container configured to facilitate perfusion.

In accordance with another aspect of the present invention, a device for collecting cord blood using perfusion includes a portable container having a chamber for receiving the placenta. The device includes a means for affixing a reservoir of perfusion fluid to the container, and a means for affixing a reservoir for collecting cord blood and perfusate to the container. The device also includes a means for coupling the container to a separate device which drives the movement of fluids to and from the aforementioned reservoir.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIGS. 4A-4D illustrate the tray loading process and additional components of the tray, according to an embodiment of the present invention.

DETAILED DESCRIPTION

Figure 1:
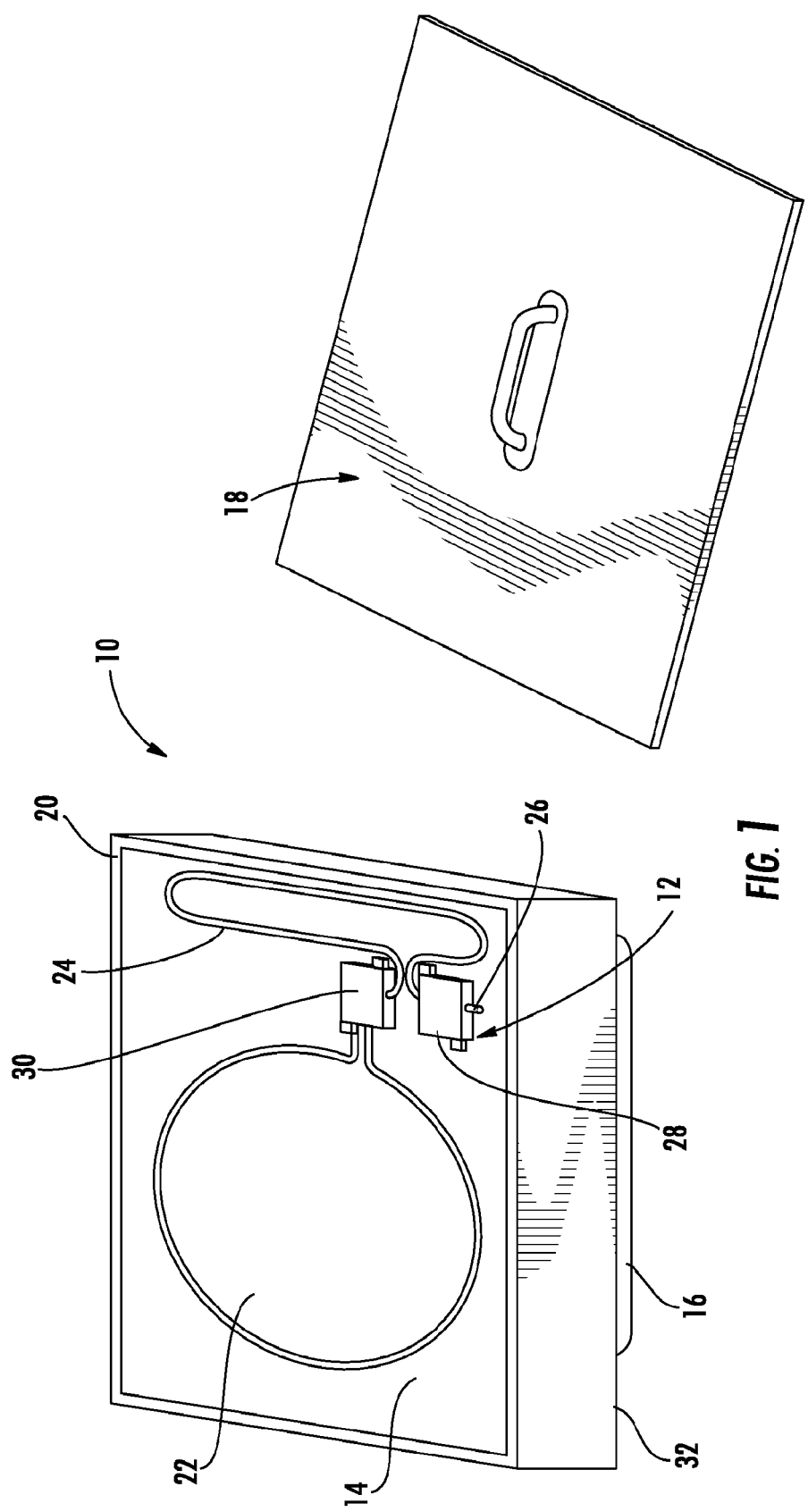
FIG. 1 illustrates a top down view of a device for collecting cord blood from an umbilical cord and placenta, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a device and method for collecting cord blood from the umbilical cord and placenta. The device includes a vascular access device, a portable tray container, and a perfusion system. It should be noted that perfusion as used throughout this application can also include an in-and-out rinse of the vasculature of the umbilical cord and placenta. The vascular access device includes two vascular access components (VACs) that clamp onto the umbilical cord (at the distal end and at the proximal end as close as possible to the placenta) at the time of delivery to accurately and guide cannulation (placement of a tube, such as a needle, into) of the vein for the purposes of perfusing the vasculature and collecting perfusate and cord blood. The device features a method for creating a simple, fast and accurate cannulation process through usage of an aiming feature on the VAC and the identification of an anatomical landmark. It also features an optimized trajectory for the cannulation of the umbilical vein.

Following delivery of the placenta and after clamping on the VACs, the placenta and VACs are placed into the portable tray container, inside corresponding cavities. The portable tray container is a closable and disposable container which features a dock for accepting the VACs and impaling the umbilical vein for vascular access. The dock is also connected to perfusate and collection bags, located on the outside surfaces of the portable tray container. The portable tray container can also include one or more sacrificial outer layers or components that are shed to preserve the cleanliness of its outer surfaces upon removal from the working area. When closed and removed from its protective outer layer, it also functions as a self-contained cartridge which is loaded into the perfusion device for processing.

Finally, the perfusion device accepts the portable tray container in a cartridge-like fashion and automates the cell capturing process by interacting with the portable tray container's bags and tubing to drive the perfusion process. The device features a simple user-interface and performs an automated protocol. Once the collection is complete, the cord blood bag is removed from the portable tray container and retained, and the portable tray container (with contents) is thrown away. The cord blood bag is compatible with existing processing chains, and the device requires minimal to no cleaning.

FIG. 1 illustrates a top down view of a device for collecting cord blood from an umbilical cord and placenta, according to an embodiment of the present invention. The device 10 includes a vascular access device 12, a portable tray container 14, and a closed perfusion system 16. The device 10 can also include a lid 18 configured to be sealed to a top surface 20 of the portable tray container 14, in order to contain the placenta and its fluids without leakage. As illustrated in FIG. 1, the portable tray container 14 is configured to receive a placenta 22 and umbilical cord 24 for perfusion and collection of the cord blood. A distal end 26 of the umbilical cord 24 is clamped in a first VAC 28, and a proximal end of the umbilical cord 24 is clamped in a second VAC 30. The first and second VACs 28, 30, will be described in more detail herein. When the VACs are secured into the tray container 14, the vasculature of the umbilical cord is connected to the closed perfusion system 16 which consists of a collection bag and perfusate bag, with associated tubing and needles, described in more detail herein. The perfusion system is positioned on the underside 32 of the tray container 14. The portable tray container 14 is closed using the lid 18 and loaded into the perfusion pump device 16, where perfusion is executed through manipulation of the closed perfusion system 16.

Figure 2A:
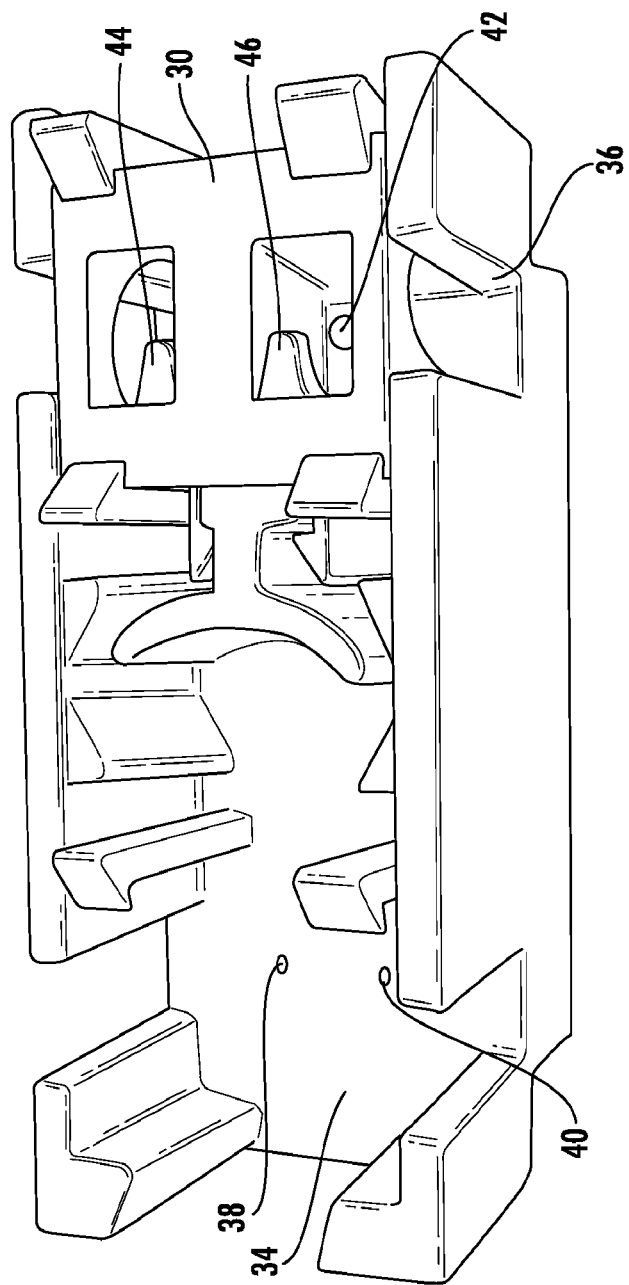
FIG. 2A illustrates a perspective view of VAC compartments and a VAC in accordance with an embodiment of the present invention.

FIG. 2A illustrates a perspective view of VAC compartments and a VAC in accordance with an embodiment of the present invention. As illustrated in FIG. 2A, VAC compartments 34, 36 can be included in the device to hold the first and second VACs 28, 30 in place. The VAC compartments 34 and 36 can be a stand-alone component that then couples to the tray container, incorporated into the tray container, or can take any other suitable form for securing the VACs 28, 30 to the tray container. The VAC compartments 34 and 36 include coupling holes 38, 40 for the needles 42 used to puncture the vein in the umbilical cord. The needles 42 can be rubber shielded, to preserve sterility, as illustrated in FIG. 2.

Further as illustrated in FIG. 2A, the VACs 28, 30 couple with the VAC compartments 34, 36 using snap fittings, although any other suitable means of coupling the two components known to or conceivable by one of skill in the art could also be used. When each VAC 28, 30 is snapped into its corresponding VAC compartment 34, 36, the umbilical cord is impaled on needles. Additionally, the VACs 28, 30 can include aiming indicators 44, 46 used to line up the umbilical vein such that it can be punctured from the opposite side by the needles 42, which are connected, on their other side, to the perfusate bag and the collection bag of the closed perfusion system. The aiming indicators 44, 46, aimed at the umbilical vein, serve as a simple, fast, and intuitive method for ensuring accurate and reliable cannulation of the vein. Both the VACs 28, 30 and the VAC compartments 34, 36 can be formed from plastic or any other suitable material known to or conceivable by one of skill in the art.

Figure 2B:
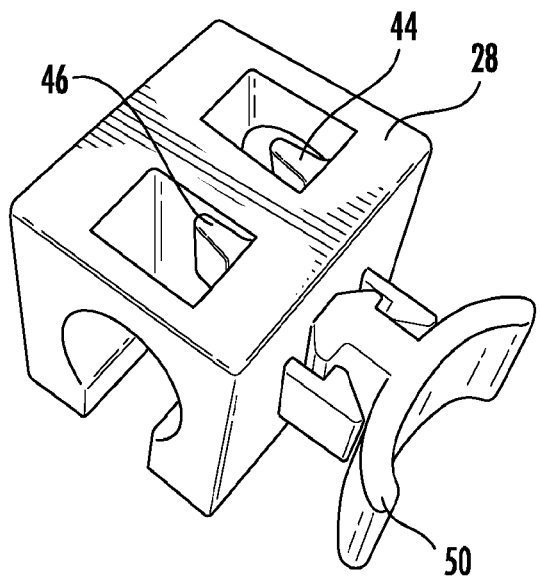
FIGS. 2B and 2C illustrate perspective views of a VAC, according to an embodiment of the present invention.
Figure 2C:
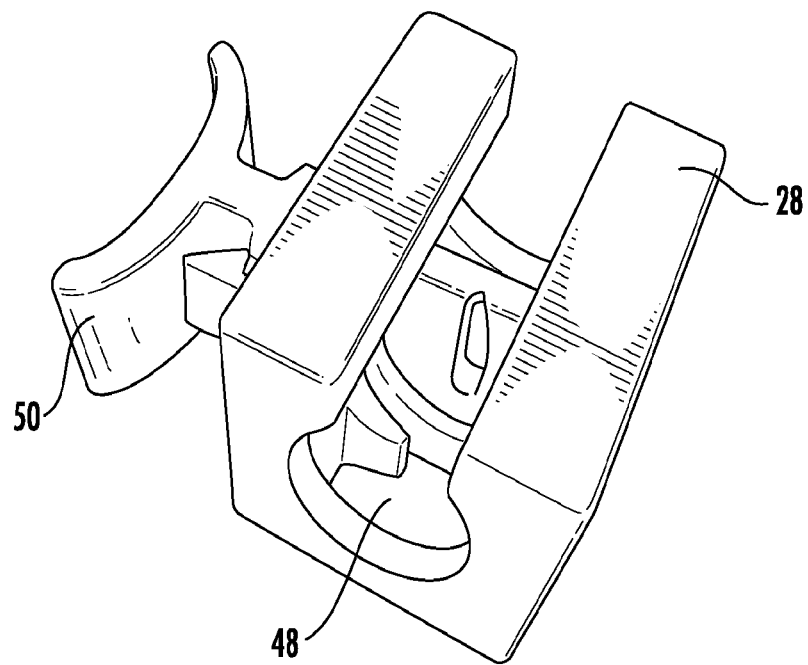

FIGS. 2B and 2C illustrate perspective views of a VAC, according to an embodiment of the present invention. As illustrated in FIGS. 2B and 2C, the VAC 28 includes a cord channel 48 and aiming indicators 44, 46. As noted above, the aiming indicators 44, 46 are lined up with the umbilical vein, after the umbilical cord is placed into the cord channel 48. The cord channel can have a diameter of approximately 11-15 mm. The aiming indicators 44, 46 can take the form of any suitable indicator, such as a crosshair, post, window, or any other indicator known to or conceivable by one of skill in the art. Once the aiming indicators 44, 46 are lined up with the umbilical vein, the clamping component 50 is activated to lock the umbilical cord in the aligned position and block the flow of blood from traversing the clamped area. The clamping component 50 can be a snap-lock, umbilical cord clamp, or any other suitable clamping means, known to or conceivable by one of skill in the art. The VACs 28, 30 can also include an antiseptic agent such as alcohol or an alcohol swab, in order to provide a means for sterilizing at least the portion of the umbilical cord that will be punctured for perfusion. If an alcohol swab is used, a pull tab can be included to allow the user to draw the wipe across the surface of the cord, easily removing the wipe and sterilizing the umbilical cord in the same motion.

Figure 2D:
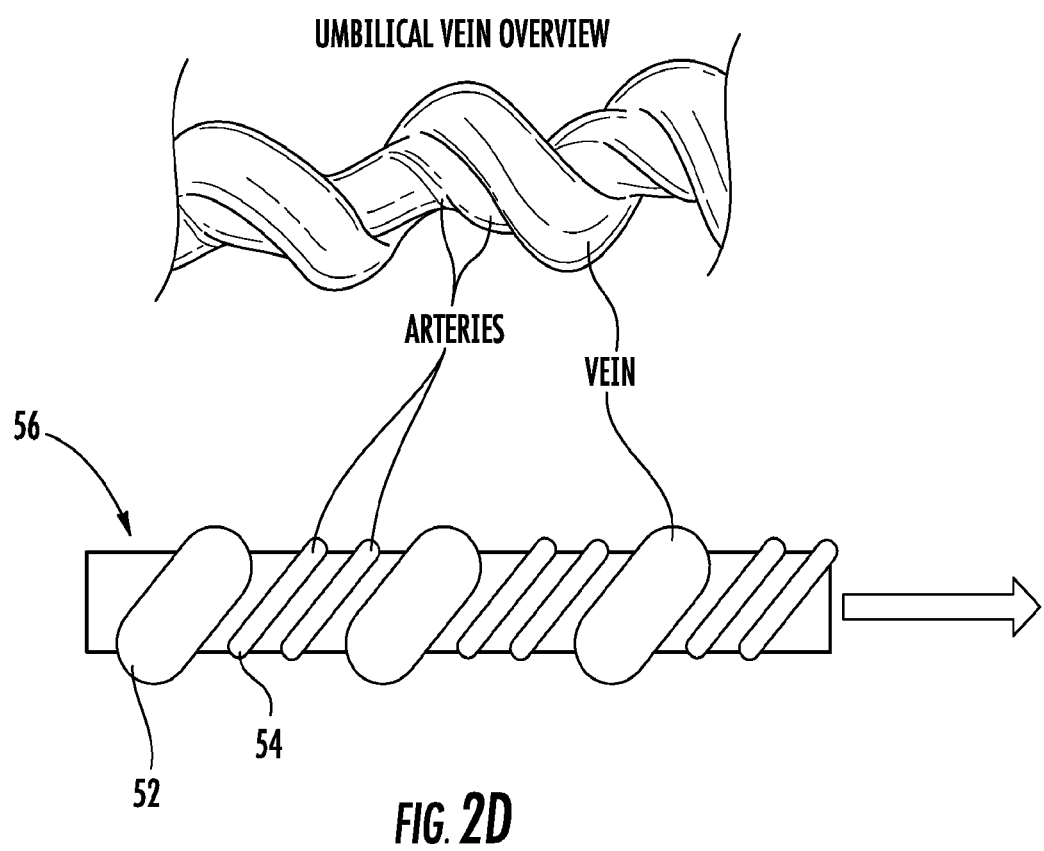
FIG. 2D illustrates a photograph and schematic diagram of the umbilical cord and its vein and arteries that will be clamped and perfused using the present invention and FIG. 2E illustrates a schematic diagram of a perfusion arrangement according to an embodiment of the present invention.
Figure 2E:
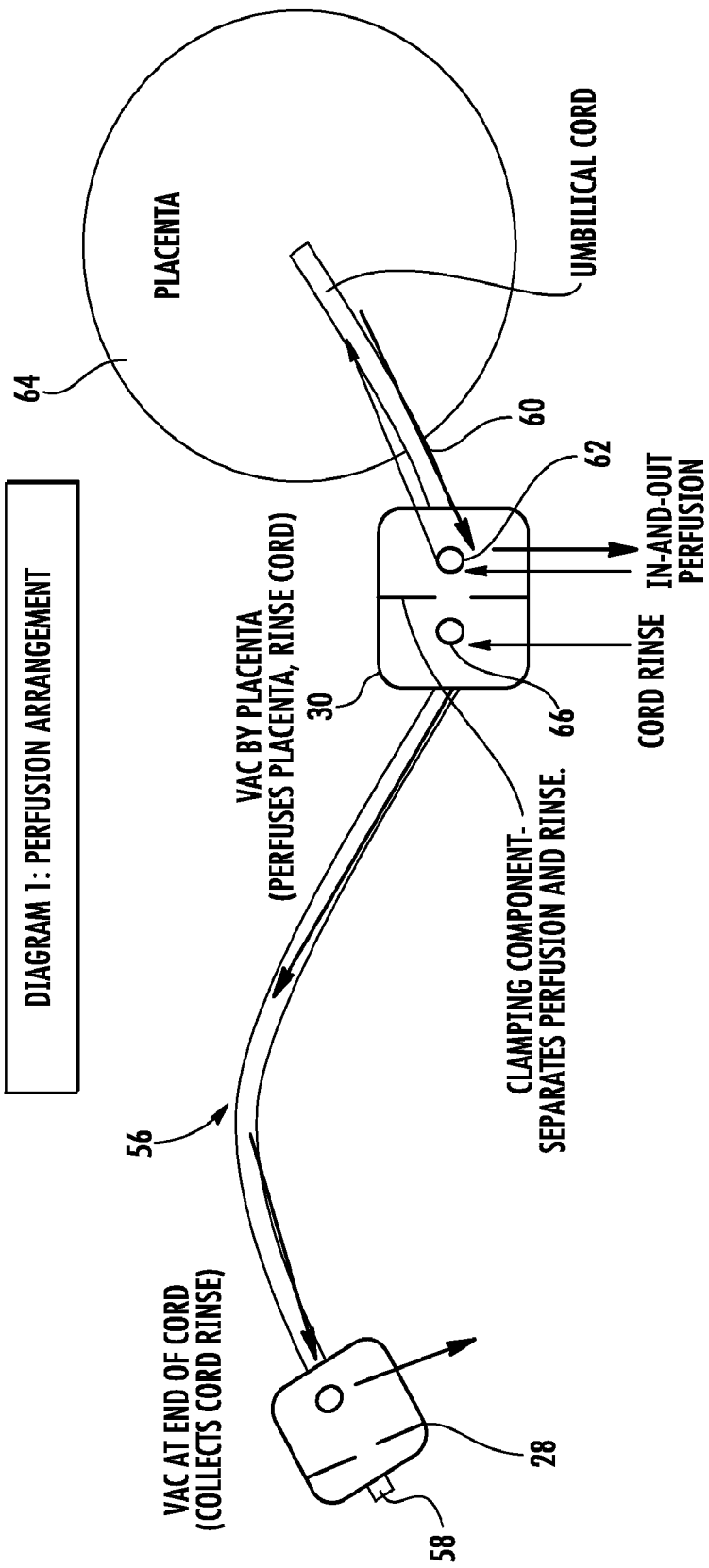

FIG. 2D illustrates a photograph and schematic diagram of the umbilical cord and its vein and arteries that will be clamped and perfused using the present invention and FIG. 2E illustrates a schematic diagram of a perfusion arrangement according to an embodiment of the present invention. As illustrated in FIG. 2D the umbilical vein 52 and umbilical arteries 54, wrap helically around the umbilical cord 56. The VACs described above with respect to FIGS. 2A-2C are clamped onto the umbilical cord 56 such that the aiming indicators also described with respect to FIGS. 2A-2C align with the umbilical vein 52. This arrangement allows the umbilical vein 52 to be punctured by the needles in the VAC compartment through the umbilical cord 56 behind the umbilical vein 52. This trajectory is used because the optimal trajectory of cannulating the umbilical vein is to pierce it through the Wharton's jelly from the opposite side, stopping approximately 0.7 mm short of piercing completely through. This avoids problems with the deformation and collapse of the umbilical vein while cannulating, as well as issues with glancing, non-penetration, and over penetration.

FIG. 2E illustrates the placement of the VACs 28, 30 on the umbilical cord 56. As illustrated in FIG. 2E, the VACs 28, 30 are clamped onto the umbilical cord 56 such that one VAC 28 is positioned at the distal or cut end 58 of the umbilical cord 56 and that the other VAC 30 is positioned at the proximal end or placental end 60 of the umbilical cord 56. The VAC 28 positioned at the distal end 58 of the umbilical cord 56 collects cord blood and perfused cells that are rinsed from the umbilical cord 56. The VAC 30 positioned at the placental end 60 of the umbilical cord 56 connects the umbilical vein to a first needle 62 that provides in-and-out perfusion of the placenta 64 and a second needle 66 that provides perfusion to rinse the cord blood from the umbilical cord to be collected by the VAC 28 positioned at the distal end 58 of the umbilical cord 56. Therefore, VAC 28 can be referred to as a one-access point VAC, as it connects only one needle of the closed perfusion system to the umbilical vein. The clamping component of the VAC 30 positioned at the placental end 60 of the umbilical cord 56 separates the perfusion of the placenta 64 and the rinse of the cord 56. Similarly, VAC 30 can be referred to as a two-access point VAC, as it connects to two needles of the perfusion system to the umbilical vein. It should be noted that the perfusion arrangement included herein is included by way of example and is not to be considered limiting. For instance it is possible that only one of the VACs 28, 30 is used to for perfusion and collection of the cord blood. Any other suitable perfusion arrangement with the VACs known to or conceivable by one of skill in the art could also be used.

Figure 3A:
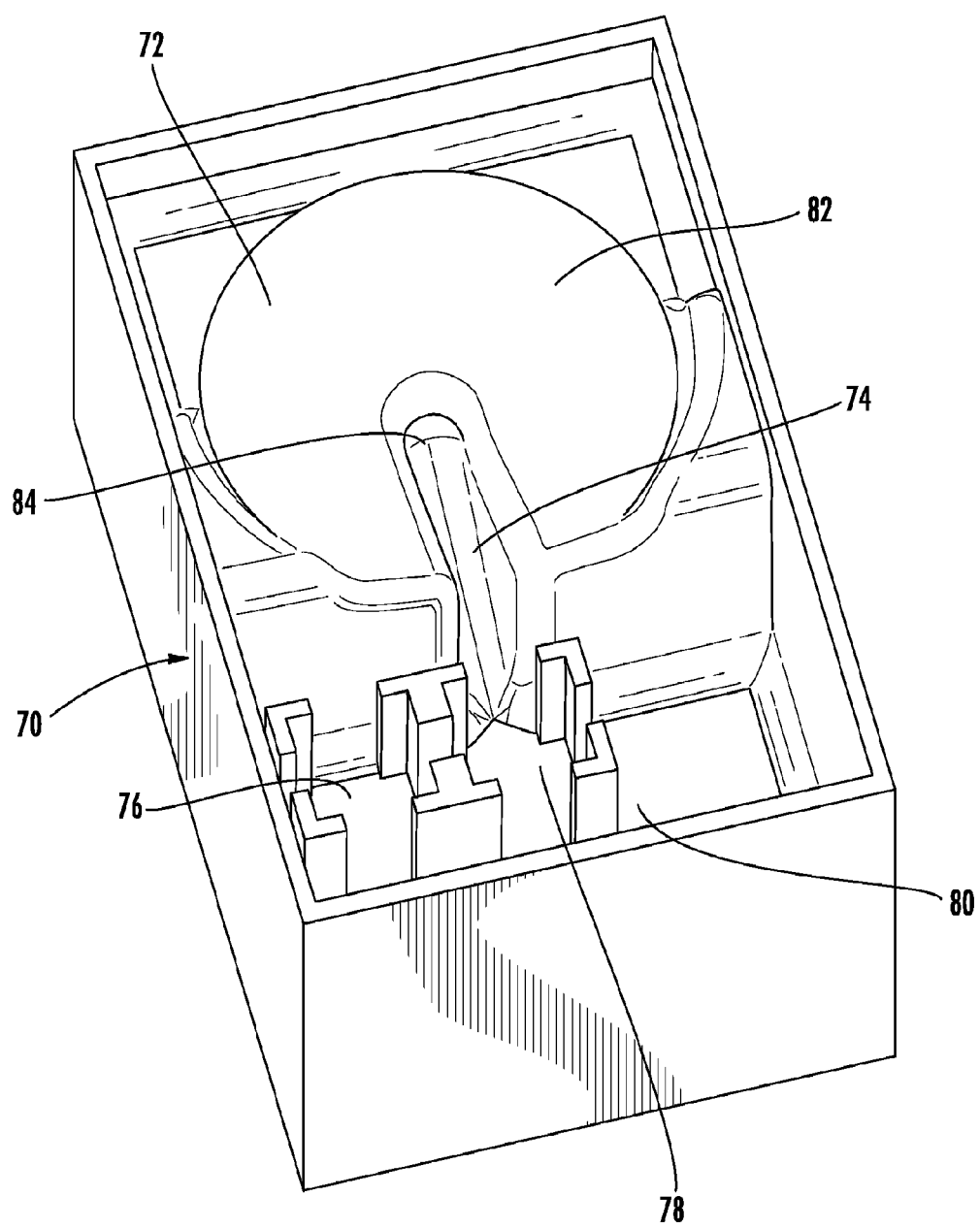
FIG. 3A illustrates a perspective view of a tray for holding the placenta and umbilical cord.
Figure 3B:
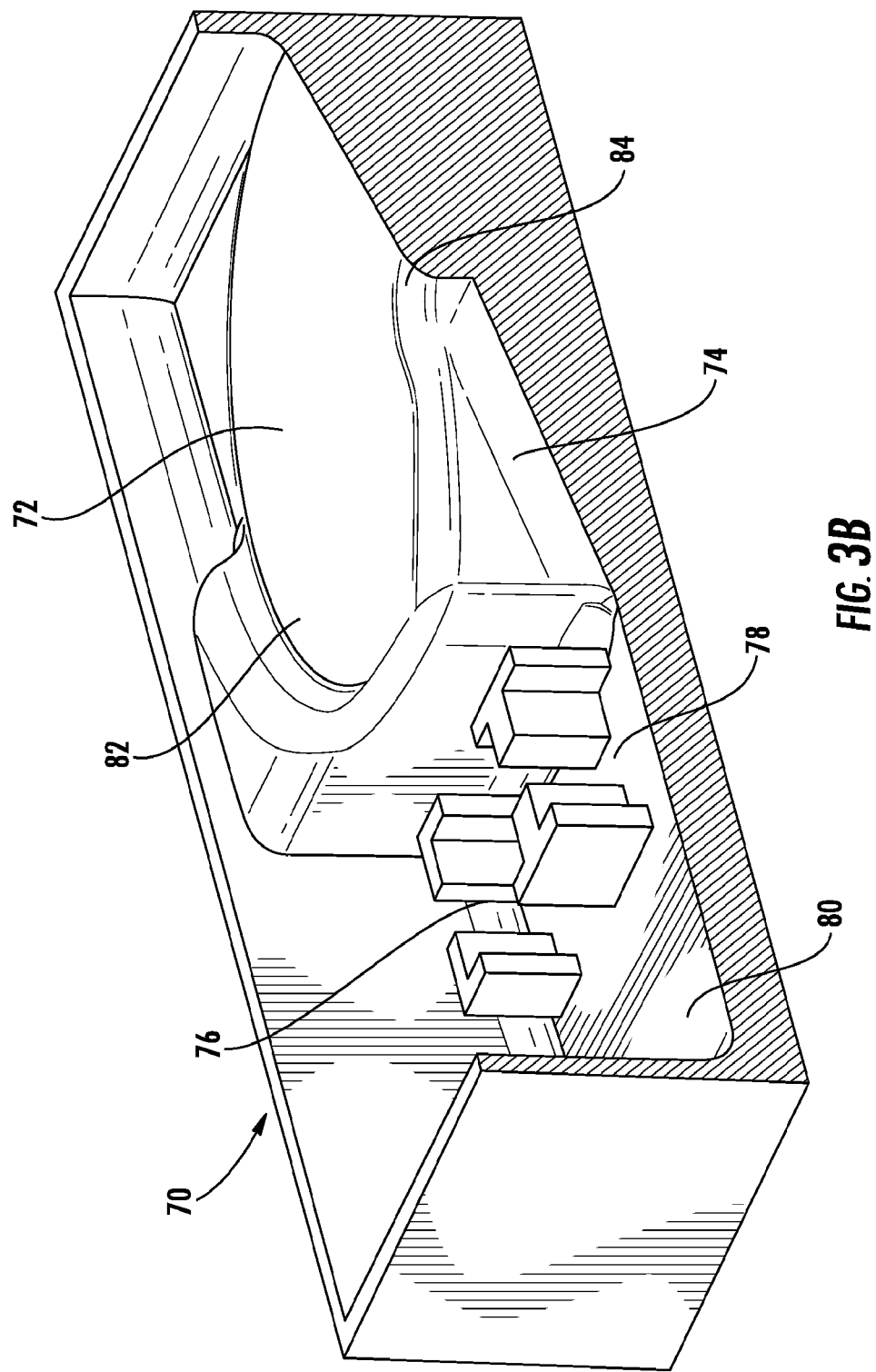
FIG. 3B illustrates a sectional view of a tray for holding the placenta and umbilical cord both according to an embodiment of the present invention.

FIG. 3A illustrates a perspective view of a tray for holding the placenta and umbilical cord, and FIG. 3B illustrates a sectional view of a tray for holding the placenta and umbilical cord both according to an embodiment of the present invention. The tray 70 is a disposable and closable holding container for the placenta once it has been delivered. The tray also carries the perfusion system, which is not illustrated here, including the perfusate bag, the collection bag, and the shielded needles. The tray 70 is approximately 8" by 12", in order to replace the disposable basin currently used in deliveries for placenta disposal.

As illustrated in FIGS. 3A and 3B, the tray 70 is partitioned and includes a placenta compartment 72, a groove 74 for the umbilical cord, VAC compartments 76, 78 and an umbilical cord compartment 80. The placenta compartment 72 includes slightly sloped sides 82 and is shaped similarly to a funnel with a gentle incline. This allows for gravity to encourage draining of placental blood towards the umbilical cord. The groove 74 for the umbilical cord is positioned in the bottom and the center of the placental compartment 72. The groove 74 is sloped slightly downwards along its length to assist the drainage of blood and allows for the cord to run out from under the placenta, to the VAC compartments 76, 78, without being compressed and potentially compromising flow of blood and perfusate through the umbilical vein. Additionally, the upper edge 84 where the groove 74 meets the placenta compartment 72 is curved to reduce the likelihood of compressing the umbilical vessels and blocking flow.

Further as illustrated in FIGS. 3A and 3B, the VAC compartments 76, 78 accept both of the VACs attached to the umbilical cord. The VAC compartments 76, 78 include rubber-shielded needles to preserve needle sterility. When each VAC is snapped into its corresponding VAC compartment, the umbilical cord is impaled on the needles. The VAC guides the needles to accurately cannulate the umbilical vein, based on the user's alignment of the aiming indicator with the umbilical vein. These needles are connected to the perfusate bag and the collection bag, positioned on the exterior of the tray. One of the VAC compartments 76 includes one access point, and is configured to couple with the one access point VAC, described above. This VAC compartment 76 includes one needle and is used to receive cord blood rinsed through the umbilical cord, as described above. The other VAC compartment 78 includes two access points and is configured to couple with the two access point VAC described above. This VAC compartment 78 includes two needles allowing in and out perfusion of the placenta through one access point and rinsing of cord blood toward the other VAC using the second access point. Additionally, the umbilical cord compartment 80 provides enough room, such that the length of the umbilical cord disposed between one VAC and the other VAC can lie within the tray 70 without kinking. This facilitates collection of cord blood by preventing blockage of fluid flow.

FIGS. 4A-4D illustrate the tray loading process and additional components of the tray, according to an embodiment of the present invention. As illustrated in FIG. 4A, the tray 100 holds the placenta 102, the umbilical cord 104, and the VACs 106, 108 clamped to the umbilical cord 104. The umbilical cord 104 can be wiped with an antiseptic wipe before being placed in the tray 100 to ensure sterility. The tray 100 also includes a gap cover film 110 disposed along and extending slightly beyond an outer edge 112 of the tray 100. The gap cover film 110 protects the outer surfaces of the tray 100 from biological fluids seeping between the tray 100 and the tray shell 118. The gap cover film 110 is removed, as illustrated in FIG. 4B, allowing the lid 116 to be attached to the tray 100. The lid 116 can be attached to the tray 100 using frictional forces or adhesive. The lid 116 is a separate component of the device, which closes the tray 100 in a leak-proof manner to contain its contents. The lid 116 is kept separate from the tray 100 and handled with clean gloves. Once attached, the lid lifts the tray 100 out of the tray shell 118, as illustrated in FIG. 4C. The lid 116 can also include a handle 120, to facilitate removal from the tray shell 118 for transport. The tray shell 118, illustrated in FIG. 4D is slightly larger than the tray 100. It is form fitting and protects the outer surface of the tray 100 from being dirtied by biological fluids, such as blood splatter or smear in handling inside the work area. It should also be noted that the lid 116 can be deformable to provide a compressive force on the placenta, for the purpose of driving the cord blood out of the placental vasculature and into the umbilical cord.

Figure 5:
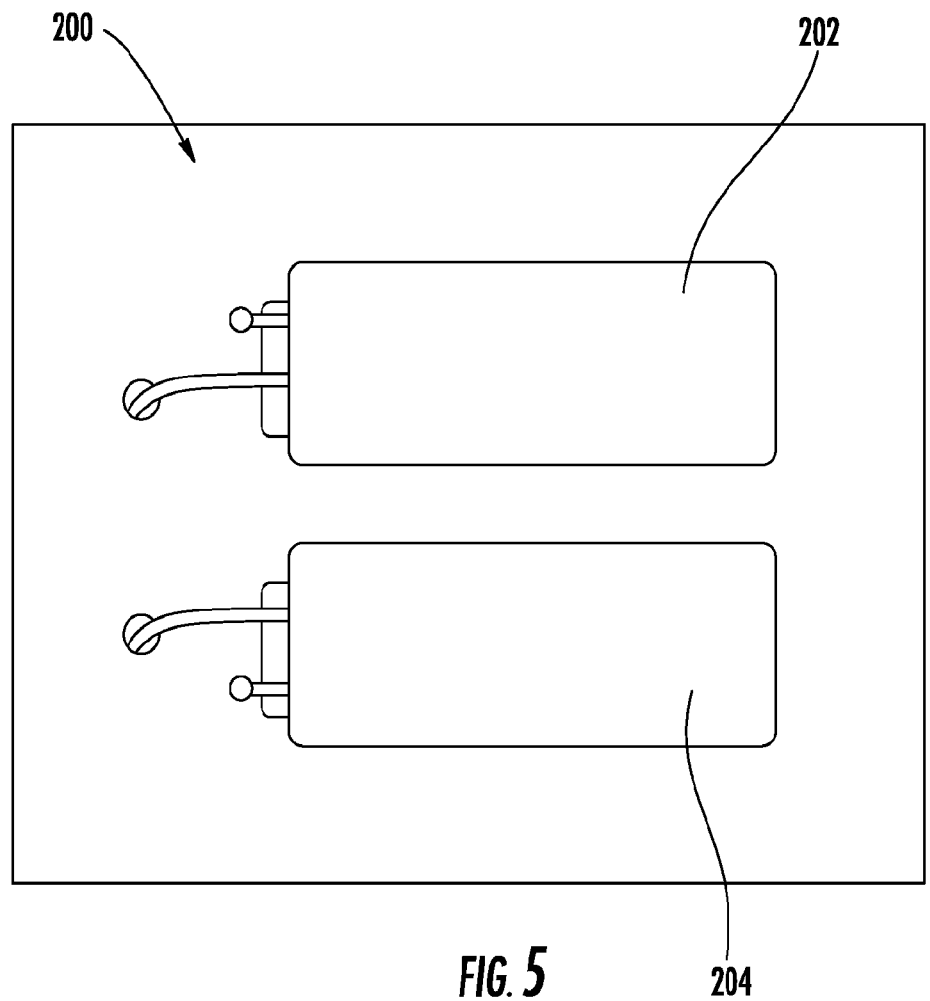
FIG. 5 illustrates the closed perfusion system for collecting the cord blood coupled to the tray, according to an embodiment of the present invention.
Figure 6:
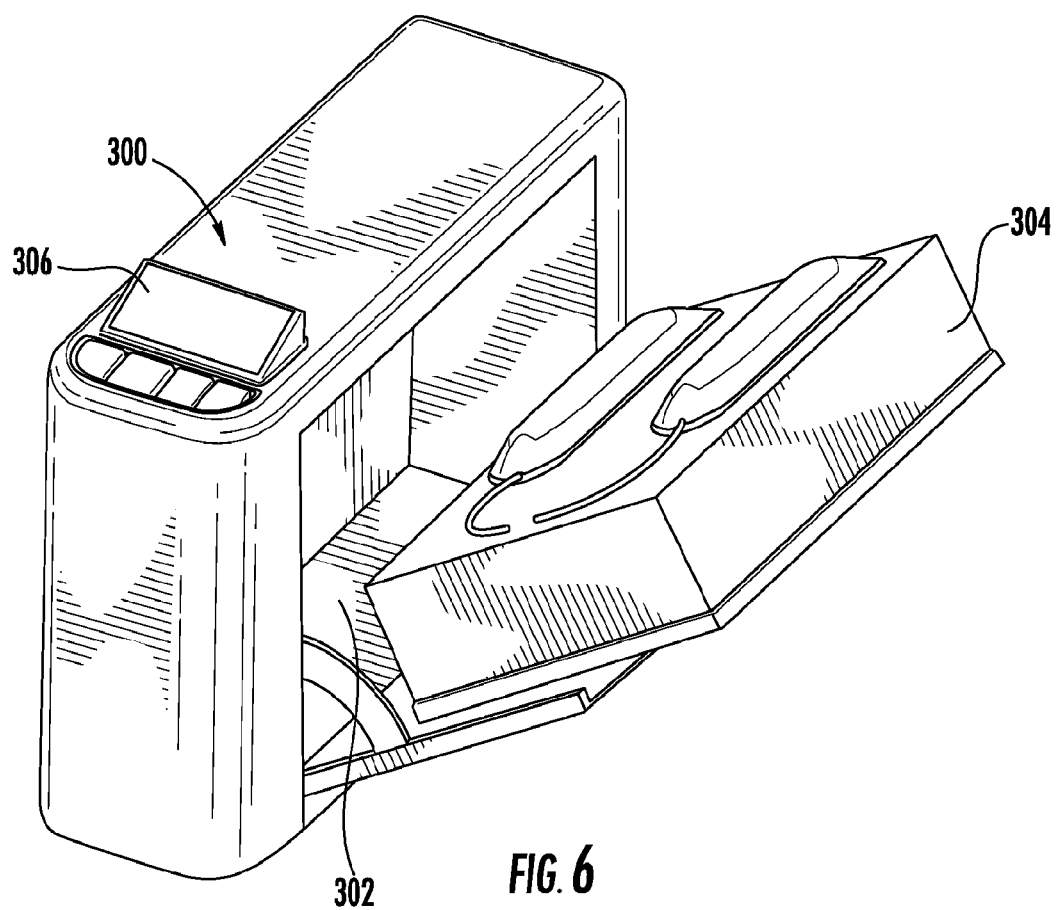
FIG. 6 illustrates a tray and a perfusion pumping system according to an embodiment of the present invention.

FIG. 5 illustrates the closed perfusion system for collecting the cord blood coupled to the tray, and FIG. 6 illustrates a perfusion pumping system, both according to an embodiment of the present invention. The perfusion system 200, as illustrated in FIG. 5, includes a perfusate bag 202 and a collection bag 204. The perfusate bag 202 stores the perfusate solution in a volume of approximately 100-450 mL. The perfusate solution can contain a saline solution and an anticoagulant, such as heparin, citrate phosphate dextrose or any other suitable anticoagulant known to or conceivable by one of skill in the art. The anticoagulant can be used in various concentrations. The collection bag 204 receives cord blood and the perfusate infused through the vasculature of the placenta and umbilical cord. The collection bag 204 is configured to hold approximately 150 ML of volume more than is contained in the perfusate bag 202. Fluid flow is diverted to and from the needles, collection bag, and perfusate bag, as necessary to perform the perfusion and rinsing protocol by typical flow-control devices known to those of skill in the art. Following perfusion protocol, the collection bag 204 is removable from the tray. The perfusate bag 202 and the collection bag 204 are coupled to the needles in the VAC compartments using typical tubing and connectors known to those of skill in the art.

The bags 202, 204 and tubing can also be configured to couple to a perfusion pumping system 300, illustrated in FIG. 6, and the perfusion pumping system's 300 pumping mechanism. Such a perfusion pumping system 300 can include peristaltic pumps that interact with the tubing or actuators to apply pressure to the perfusate bag, a compression mechanism for compressing the lid to apply pressure to the placenta, actuators to control fluid flow in the perfusion system, and a linear actuator that can actuate the components through a deformable portion of the tray wall. Such a system can also include a tray compartment 302, such that the tray 304 can be accepted and ejected in a cassette-like fashion, and an antiseptic reservoir, with contents that are pumped into the tray to clean the surface of the cord prior to cannulation. An electronic interface 306 can be provided for the operation of the perfusion pumping system 300. Additionally, the perfusion pumping system 300 can implement a low-cell volume discard protocol that allows the device to reduce dilution of the final product. Depending on the volume of perfusate used, delay before collection of perfusate, and number of previously executed perfusions a portion of the initial volume can be discarded, as it will contain few cells.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A device for collecting cord blood, comprising:
   a first vascular access component configured to be clamped on an umbilical cord;
   a tray defining a first chamber for receiving a placenta and a second chamber for receiving the first vascular access component, wherein the second chamber is configured to hold needles to puncture umbilical vessels for perfusing the placenta and umbilical cord and collecting the cord blood, and wherein the tray comprises a third chamber; and
   a second vascular access component configured to be clamped on the umbilical cord and configured to be received by the third chamber, wherein the second vascular access component comprises two access points, and wherein the third chamber for receiving the second vascular access component comprises two needles.

2. The device of claim 1, wherein the first vascular access component is configured to be clamped at a distal end of the umbilical cord.

3. The device of claim 1 wherein the second vascular access component is configured to be clamped at a proximal end of the umbilical cord, and positioned adjacent to a junction of the umbilical cord and the placenta attached to the umbilical cord.

4. The device of claim 1 wherein the third chamber is configured to hold needles to puncture the umbilical vessels for perfusing the placenta and umbilical cord and collecting the cord blood.

5. The device of claim 1 wherein the first and second vascular access components comprise aiming indicators to align with an anatomical feature of the umbilical cord.

6. The device of claim 5 wherein the anatomical feature further comprises an umbilical vein.

7. The device of claim 5 wherein the aiming indicators comprise one or more features chosen from a group consisting of a crosshair, a post, and a window.

8. The device of claim 1 wherein the first vascular access component comprises one access point.

9. The device of claim 8 wherein the second chamber for receiving the first vascular access component comprises one needle.

10. The device of claim 1 further comprising a perfusion bag and a collection bag.

11. The device of claim 10 wherein the perfusion bag contains a saline solution and an anticoagulant.

12. The device of claim 11 wherein the anticoagulant comprises one selected from a group consisting of heparin and citrate phosphate dextrose.

13. The device of claim 1 wherein the device further comprises a lid.

14. The device of claim 13 wherein the tray comprises a means to seal the lid to the device.

15. The device of claim 13 wherein the lid is configured to be deformable to provide a compressive force on the placenta for the purpose of driving cord blood out of the placental vasculature and into the umbilical cord.

16. The device of claim 1 wherein the first chamber for receiving the placenta comprises sloped walls.

17. The device of claim 1, further comprising a removable tray shell, such that any contamination can be removed and disposed of before perfusion.

18. The device of claim 1 wherein the tray is configured to be coupled to a device for driving the perfusion process.

* * * * *